United States Patent
Farrell et al.

(10) Patent No.: US 9,625,437 B2
(45) Date of Patent: Apr. 18, 2017

(54) SYSTEM FOR DETERMINATION OF EXPLOSIBILITY INDICIES OF FUELS

(71) Applicant: Fike Corporation, Blue Springs, MO (US)

(72) Inventors: Tom Farrell, Lawrence, KS (US); Stuart Johnson, Oak Grove, MO (US)

(73) Assignee: Fike Corporation, Blue Springs, MO (US)

( * ) Notice: Subject to any disclaimer, the term of this patent is extended or adjusted under 35 U.S.C. 154(b) by 76 days.

(21) Appl. No.: 14/671,856

(22) Filed: Mar. 27, 2015

(65) Prior Publication Data

US 2015/0276701 A1    Oct. 1, 2015

Related U.S. Application Data

(60) Provisional application No. 61/972,108, filed on Mar. 28, 2014.

(51) Int. Cl.
*G01N 33/22* (2006.01)

(52) U.S. Cl.
CPC ........... *G01N 33/22* (2013.01); *G01N 33/227* (2013.01)

(58) Field of Classification Search
CPC .... G01N 33/22; G01N 33/222; G01N 33/225; G01N 33/227
USPC .............................................. 73/35.14–35.17
See application file for complete search history.

(56) References Cited

U.S. PATENT DOCUMENTS

| | | | |
|---|---|---|---|
| 8,950,245 B2 * | 2/2015 | Tomita | F02D 41/005 73/35.02 |
| 2006/0234387 A1 | 10/2006 | Schaeffer | |
| 2007/0239345 A1 * | 10/2007 | Bizub | G01N 33/2829 701/114 |
| 2009/0025689 A1 | 1/2009 | Ruggiano et al. | |
| 2011/0168129 A1 | 7/2011 | Kurtz et al. | |
| 2012/0185151 A1 | 7/2012 | Shibata et al. | |
| 2012/0318054 A1 * | 12/2012 | Tomita | F02D 41/005 73/114.45 |

FOREIGN PATENT DOCUMENTS

EP    1793110    6/2007

OTHER PUBLICATIONS

Standard Test Method for Eplosibility of Dust Clouds; ASTM E1226-12a (Jan. 2013).*
The International Search Report and Written Opinion dated Jul. 30, 2015, in PCT/US15/023137 filed Mar. 27, 2015.

* cited by examiner

*Primary Examiner* — Daniel S Larkin
*Assistant Examiner* — Nathaniel Kolb
(74) *Attorney, Agent, or Firm* — Hovey Williams LLP (57) ABSTRACT

Explosion test systems for determining explosibility indicies (Kst) of certain dust and gaseous fuels are provided. The test systems comprise a combustion vessel (130) and associated control equipment (110) containing software for operating the combustion vessel and collecting data generated thereby. The combustion vessel (130) generally comprises a test chamber (140) and a reservoir module (150) operable to inject a fuel into the test chamber, wherein an ignition module (170) ignites the fuel.

36 Claims, 9 Drawing Sheets

SYSTEM FOR DETERMINATION OF EXPLOSIBILITY INDICIES OF FUELS

RELATED APPLICATION

This application claims the benefit of U.S. Provisional Patent Application No. 61/972,108, filed Mar. 28, 2014, which is incorporated by reference herein in its entirety.

BACKGROUND

The present invention relates generally to explosion test systems. More specifically, the present invention concerns an improved real-time system for determining explosibility indices of certain fuels, especially dust fuels and gaseous fuels.

DISCUSSION OF THE PRIOR ART

Combustible dusts such as grain dusts, coal dusts, flour, and wood dusts, are fine particles that present an explosion hazard in workshops or facilities when suspended in air under certain conditions. A "dust fuel" explosion can cause catastrophic loss of life, injuries, and destruction of buildings. Explosion testing is used to quantify the maximum pressure of a dust cloud explosion (Pmax) and the volume-scaled maximum rate of pressure rise (Kst). The Kst value and Pmax, among other properties, are explosive properties measured in the laboratory to quantify the severity of a dust explosion. Testing dust fuel explosibility to determine the Kst value and Pmax is essential for any type of safety equipment design related to dust fuel explosibility. More particularly, manufacturers use these values to validate the design of protection systems (i.e., explosion venting, explosion suppression and containment systems). Explosibility tests are useful in determining the "class" in which a dust sample falls within, which is generally helpful in guiding service providers with analyzing their facilities or with designing safety measures for the facilities.

The tests are generally carried out in a 20 liter sphere apparatus which reproduces a high state of turbulence to simulate worst case process plant conditions. A weighed quantity of combustible dust is placed into a dust container. The main explosion chamber is then evacuated to 0.4 bar absolute. An automatic test sequence is initiated to pressurize the dust container to 20 bar gauge, and then a fast acting ball valve on the dust container outlet is opened to allow material into the explosion chamber. The control system activates igniters within the sphere within a predetermined period of time, 65 ms for example, after the dust has been dispersed.

Typically, tests are carried out over several series to ensure a thorough investigation of the explosion properties. However, tests have generally shown a large variance in Kst values from these systems. More particularly, fault can be attributed to the ball valve response time, wherein test results have shown approximately 20% in ball valve response time variability. In many circumstances, the ball valve may inadvertently be at least partially open at the time of combustion, thereby increasing the sphere volume by approximately 1 liter, a 5% variation in system volume.

Further contributing to inaccurate test results are limitations inherent in conventional testing software and operating systems. Conventional test systems have used PC software that synchronously controlled injection and ignition signals, wherein each injection and ignition event was based on a fixed time. For example, the system will initiate the injection at start time "T[0]" and will ignite the dust fuel at ignition time "T[D]". Typical ball valve response times can typically vary somewhere between 30-75 ms. Problematically, these systems could not compensate for variances in injection system response times, which result in significant changes in turbulence levels within the explosion chamber.

Turbulence of dust fuels in the test environment is important because it has a strong effect on the Kst value. More particularly, when the time delay "T[D]" is short, the turbulence of the test chamber atmosphere will be greater, resulting in a higher reported Kst value. On the other hand, when the time delay is longer, the turbulence of the test chamber atmosphere is lower, resulting in a lower reported Kst value. In an ideal test environment, the turbulence is predictable and controlled based on actual injection-ignition time delays.

Variations in test data resulting from varying test conditions (i.e., inadvertently increased sphere volume and delayed injection times) can lead to over or under specification in safety system design. For example, test data that inaccurately reports low Kst values may result in the under specification of safety systems, which could lead to catastrophic safety system failure. On the other hand, test data inaccurately reporting high Kst values may result in the over design of safety systems, leading to material inefficiency and overspending. It is crucial to obtain accurate results and provide accurate test data to maximize the effectiveness of safety systems in light of the known dangers related to the explosibility of dust fuels.

In light of the above, a dust fuel explosibility test system is needed wherein a fairly consistent level of turbulence in dust fuels is achieved. Eliminating the problem of variable delays due to injector valve response time can be achieved by measuring the time delay value "T[D]" from the actual time of injection as opposed to the commanded time of injection. The utilization of pressure sensors within the system may facilitate the determination of actual injection times occurring within the test system. The use of multi-tasking operating systems, such as Windows, should not be used for such time-sensitive decision-making algorithms. Preferably, a real-time operating system is used to detect pressure changes and further manage time-critical events in the test system.

SUMMARY OF THE INVENTION

In one embodiment of the present invention, there is provided a non-transitory computer-readable storage medium with an executable program stored thereon for determining explosibility indices of fuels, such as dust fuels, in a combustion vessel. The program broadly instructs the processor to perform the following steps: (1) inject fuel into a test chamber of the combustion vessel; (2) detect an injection of the fuel; (3) command the injection valve to close; (4) start a timer simultaneous to or subsequent to any of steps (1), (2), or (3); and (5) ignite the fuel. Alternatively, in lieu of a timer to control ignition, the program can instruct the processor to collect data regarding the instantaneous turbulence within the test chamber and control ignition based upon detection of a predetermined instantaneous turbulence value.

In another embodiment of the present invention, there is provided a method of determining explosibility indices of fuels, such as dust fuels. The method broadly comprises the steps of: (1) injecting a fuel into a test chamber by opening an injection valve; (2) detecting injection of the fuel by sensing a change in pressure; (3) commanding the injection valve to close; (4) starting a timer generally simultaneous to or subsequent to any of steps (1), (2), or (3); and (5) igniting the fuel upon the timer substantially reaching a predetermined time delay value. Alternatively, in lieu of starting a timer to ignite the fuel, the method can comprise utilizing a turbulence detector for detecting the instantaneous turbulence intensity with the test chamber and then ignite the fuel upon detection of a decay in the turbulence intensity to a predetermined value.

In yet another embodiment of the present invention, there is provided a system of determining explosibility indices of a fuel, such as a dust fuel. The system comprises one or more combustion vessels and one or more corresponding remote computing devices. Each combustion vessel includes a test chamber, a pressurizable fuel discharge reservoir module having an injection valve, at least one pressure sensor, and a fuel ignition module for igniting the fuel. Each remote computing device includes a processor and a memory for storing at least a time delay value, a network interface module, and a field programmable gate array module. The field programmable gate array module operates a timer and is operably connected to the combustion vessel. Alternatively, the system may comprise a turbulence detector for detecting the instantaneous turbulence within the test chamber. The fuel ignition module can be activated based up detection of a decay in the instantaneous turbulence intensity with the test chamber to a predetermined value.

The drawing figures do not limit the present invention to the specific embodiments disclosed and described herein.

The drawings are not necessarily to scale, emphasis instead being placed upon clearly illustrating the principles of the invention.

DETAILED DESCRIPTION

The following detailed description is not to be taken in a limiting sense. The embodiments described herein are intended to describe aspects of the invention in sufficient detail to enable those skilled in the art to practice the invention. Other embodiments can be utilized and changes can be made without departing from the scope of the invention. Embodiments of the present invention are broadly directed to a system, method, and computer program (collectively the "invention") for determining explosibility indices of various dust and/or gaseous fuels, and more particularly to systems and methods that control, in real-time, testing modules related to the testing of fuel explosibility indices.

The invention may comprise computing devices, servers, databases, and communications networks to facilitate the functions and features described herein. The computing devices and servers may comprise any number and combination of processors, controllers, integrated circuits, programmable logic devices, or other data and signal processing devices for carrying out the functions described herein, and may additionally comprise one or more memory storage devices, transmitters, receivers, and/or communication busses for communicating with the various devices of the system. In various embodiments of the invention, the computing devices may comprise a memory element, a communication component, a display, and/or a user interface.

In embodiments of the invention, the computing devices and/or databases may implement the computer program and/or code segments of the computer program to perform some of the functions described herein. The computer program of the present invention is stored in or on computer-readable medium residing on or accessible by the user device and/or remote for instructing the user device and/or remote device to operate certain steps of the present invention as described herein. The computer program preferably comprises an ordered listing of executable instructions for implementing logical functions in the user device and/or remote device. Portions of the computer program stored on the memory of the user device and/or remote device can be updated via a computer readable medium, a communications network, or a manual connection. Therefore, the discussion of the computer program herein is to be understood as all code segments, either individually or collectively, that are executed to implement the steps and features described herein.

The computing device may be any computing device such as a network computer running iOS, Apple OS X Server, Apple OS X, Windows, Novel Netware, Linux, UNIX, Android, Chrome, LabVIEW, any network operating system, or any real-time embedded operating system. In some embodiments, the computing device includes its own processor and memory and is housed in a separate housing. The user device may be connected to another remote device operated by an administrator of the remote device via another communications network. In other embodiments, the remote device may be a plurality of computing devices. In various embodiments, the remote device may comprise a display and/or a user interface.

Figure 1:
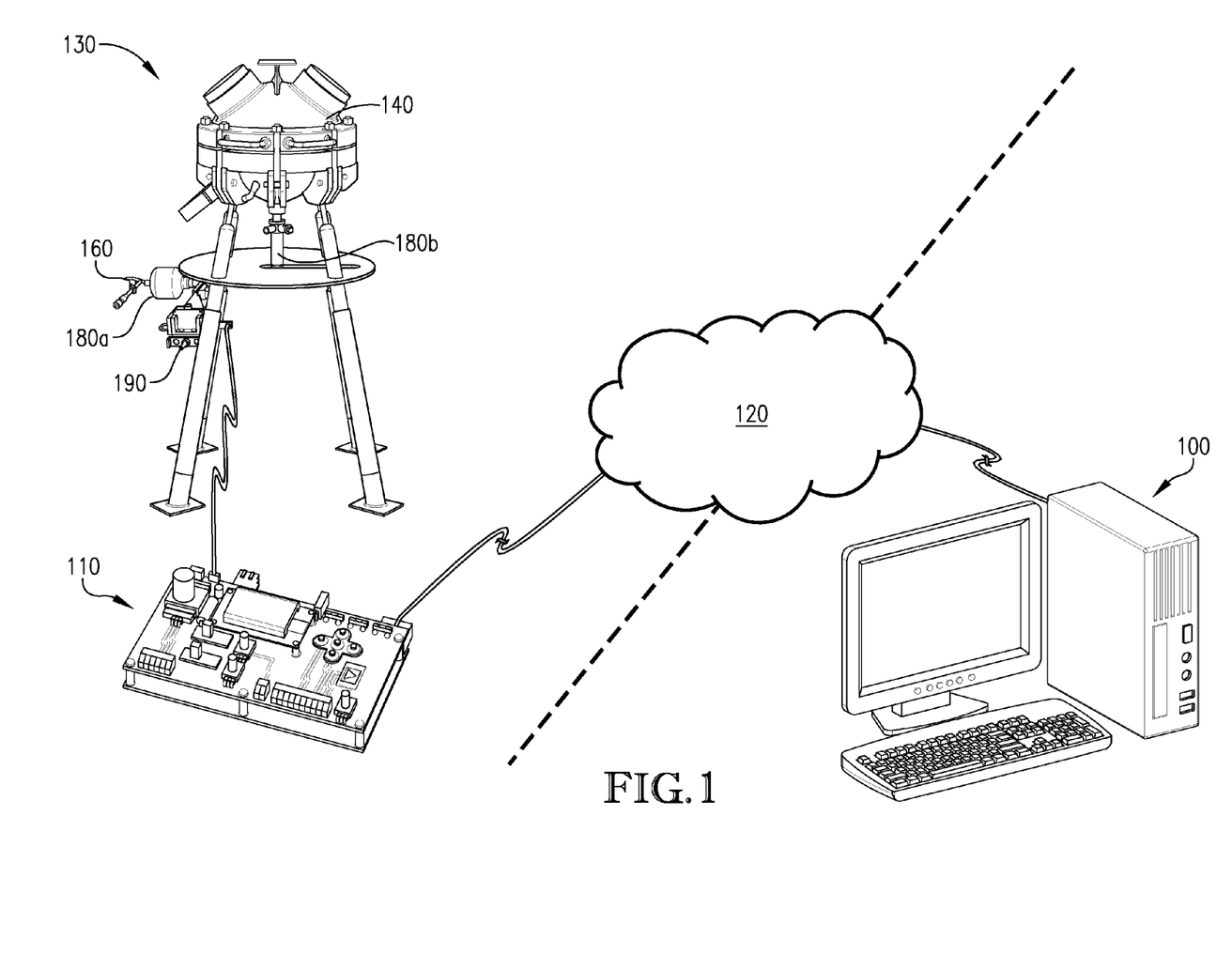
FIG. 1 is a schematic depiction of a system configured for providing improved safety and remote testing of explosibility of various fuels in accordance with an embodiment of the present invention.

Turning now to FIG. 1, the user device 100 can be any form of computing device, such as a desktop computer, laptop, tablet, smartphone, wearable computing device, or smart television. The user device 100 includes a user interface for receiving a user input, such as a button or buttons, keyboard, keypad, mouse, remote control, video game controller, microphone, accelerometer, or touch screen. The user device 100 includes circuitry and/or computer code for transmitting the signal, request, command, or other data to the remote device 110 over a network 120. The circuitry may include a modem, router, antenna, wireless transmitter, or other components for connecting to a network. The user device 100 may also be configured to receive data from the network 120 and may further include a display screen for displaying the data. The display screen may also be a touch screen for receiving the input.

The remote device 110 may be a desktop computer, laptop, tablet, smartphone, server, embedded computing device, or other device capable of running processes and connecting to a network and may include circuitry and/or computer code for triggering a programmed event or procedure. The network 120 may be the Internet, an intranet, or a telecommunications network. The remote device 110 may be any derivation of the user device 100, operable to store and host data. The remote device 110 is operable to receive and send data packets from and to a user device 100 via a communications network 120, such as the Internet, a Wi-Fi link, Bluetooth, a radio-frequency ("RF") link, or directly via a manual connection, such as a universal serial bus ("USB"), and Ethernet port. The remote device 110 may have an integrated field programmable gate array (FPGA) and memories acting as caches, e.g., SRAM, SDRAM, and so forth, connected to the computing device. The remote device 110 and FPGA may also be in communication with an integrated series of reconfigurable input/output (I/O) ports, daughter cards, and/or peripherals (e.g., USB, RS232, RS485, CAN, SD, and Ethernet) for performing a variety of functions as further discussed herein. For example, the National Instruments' reconfigurable input/output (RIO) architecture comprising a real-time processor, reconfigurable FPGA and analog and digital I/O is a remote device 110 within the scope of the invention.

Figure 2A:
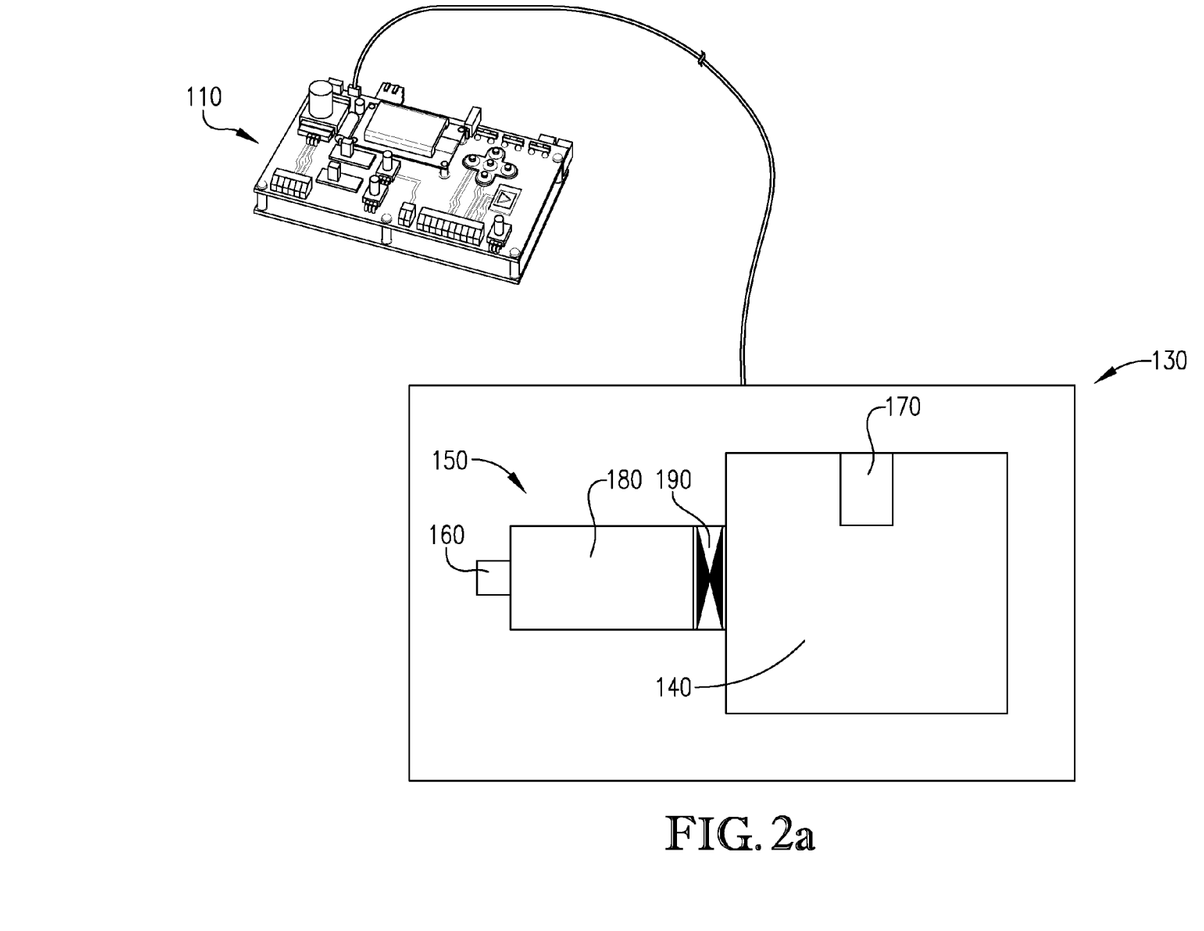
FIG. 2a is a schematic depiction of a system for providing improved testing of explosibility of dust fuels in accordance with another embodiment of the present invention.
Figure 2B:
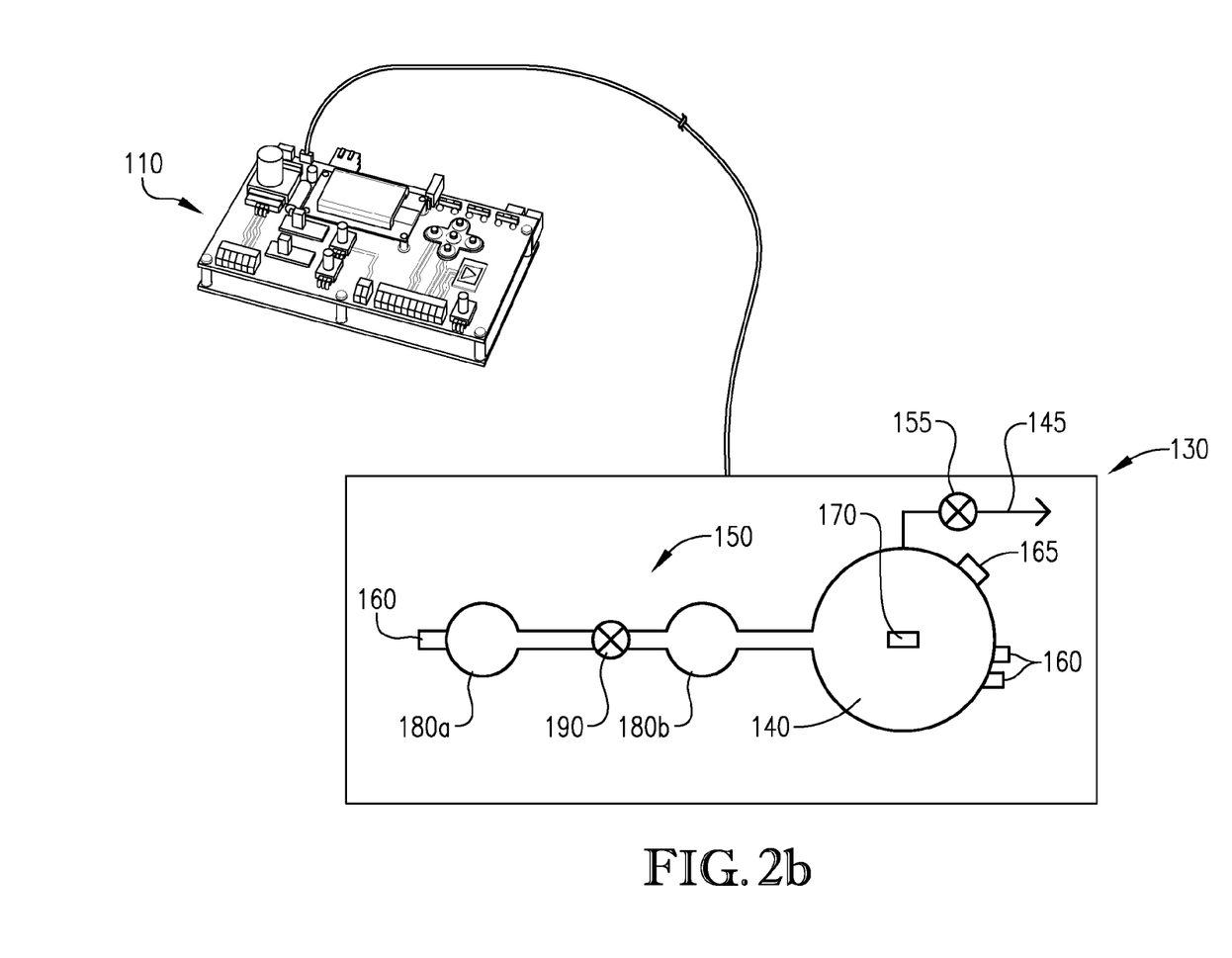
FIG. 2b is a schematic depiction of an alternate system for providing improved testing of explosibility of dust fuels in accordance with another embodiment of the present invention.

The user and/or remote device 100, 110 may be in direct or indirect communication with an explosibility test apparatus also known as a combustion vessel 130. FIGS. 2a and 2b depict alternate embodiments of combustion vessel 130 configured primarily to test explosibility of dust fuels, although the embodiments share many common components. Generally, the combustion vessel 130 is comprised of a main test chamber 140, a pressurizable dust fuel discharge reservoir module 150, at least one pressure sensor 160, and a dust fuel ignition module 170. More specifically, the test chamber may be comprised of one or more modules used for determining the explosibility indices of dust fuels, wherein each component performs one or more steps of the testing process initiated by the computer program. Components of the test chamber may be operable to communicate with the user and/or remote device 100, 110 through the network 120 or through a wired connection. In some embodiments, the components may include a sensor module for sensing conditions (e.g., pressure, open/closed state, temperature) of the test chamber and its components.

The pressure sensors 160 may be configured to constantly or periodically detect pressure within the chamber and/or the reservoir module, and further send that data to the user and/or remote computing device. In some embodiments, there may be multiple pressure sensors 160 configured to measure, in real-time, maintenance, increase, or decrease in pressure within the chamber and/or reservoir module. As one of ordinary skill in the art may appreciate, the pressure sensors 160 may be operably connected to the computing devices via hardwire or through the network 120. Pressure sensors 160 utilized in dust fuel explosibility tests, such as pressure transducers, are generally well known to one of ordinary skill in the art and will not be described further herein. In the embodiment of FIG. 2a, pressure sensor 160 is located within the reservoir module. However, the embodiment of combustion vessel 130 of FIG. 2b, vessel 130 comprises a plurality of pressure sensors 160. In particular, one pressure sensor 160 is located within reservoir module 150 and configured to measure the pressure of a discharge pressure reservoir 180a. Additionally, two pressure sensors 160 are disposed in communication with test chamber 140 and are configured to measure the pressure therein. The pressure sensors in communication with test chamber 140 are operable to detect injection of the dust fuel into chamber 140 and measure pressure development within chamber 140 upon ignition of the dust fuel.

With respect to the embodiment depicted in FIG. 2a, the dust fuel discharge reservoir module 150 (or "injection" module) may include a dust fuel chamber 180 and a valve 190, wherein the dust fuel chamber 180 can be configured to store dust fuels at a predetermined pressure. Dust fuels may generally include combustible dusts such as coal dust, saw dust, grain dust, flour, powdered metals, etc. The valve 190, preferably a ball valve or a shuttle valve, may be configured to open upon receiving a command or signal to inject the dust fuels into the main test chamber 140 and may subsequently close automatically or upon receiving a command or signal. In a preferred embodiment, closure of the valve 190 assures that the volume of the main test chamber 140 is independent and no longer in communication with the volume of the injector module 150.

With respect to the embodiment depicted in FIG. 2b, the dust fuel discharge reservoir module 150 comprises a dust fuel chamber 180b that can be charged with a dust fuel by a user. Charging of chamber 180b may also be automated and controlled by user and/or remote device 100, 110. Valve 190 is disposed in between discharge pressure reservoir 180a and dust fuel chamber 180b. Operation of valve 190 is essentially the same as its counterpart of FIG. 2a, described above. Upon opening of valve 190, pressurized gas is delivered from discharge pressure reservoir 180a, expelling the dust fuel from chamber 180b and delivering the dust fuel and pressurized gas into test chamber 140, which is initially under vacuum conditions.

The ignition module 170 may broadly include an igniter, wherein the igniter is operable to ignite the dust fuels in the test chamber 140. The igniter may be configured to fire upon receiving a command or signal to ignite the dust fuels within the vessel. Ignition modules may include an igniter, such as a heated coil, a chemical igniter, a spark generator, or a flame generator. Generally, such igniters generate enough heat to ignite the dust fuel upon contact of the heat source. Ignition modules 170 in the field of explosibility test chambers 140 are well known in the art and will not be discussed further herein.

The test chamber 140 may also be coupled to a vacuum source 145 that is operable, upon opening of valve 155, to evacuate the contents of chamber 140. In certain embodiments of the present invention, it is desirable to place chamber 140 under vacuum conditions so that the dust fuel from chamber 180b and pressurized gas from discharge pressure reservoir 180a will be the only contents present within chamber 140 upon activation of ignition module 170. The pressure sensors 160 located within test chamber 140 can be used to verify the vacuum conditions within the test chamber, at which time valve 155 may be closed.

As illustrated in FIG. 2*b*, test chamber 140 may further comprise a turbulence detector 165 that is operable to measure the instantaneous turbulence within the test chamber. As explained further below, the turbulence detector may be used in the control of ignition module 170 so that fuel ignition occurs only after a desired instantaneous turbulence intensity is achieved within test chamber 140. In certain embodiments, the turbulence detector may comprise a device employing laser Doppler velocimetry or laser Doppler anemometry for detecting particle velocity within test chamber 140. Thus, turbulence detector may comprise a laser which emits one or more laser beams into test chamber 140 and receiving optics comprising one or more photodetectors for capturing light reflected from particles within the test chamber. The reflected light fluctuates in intensity, the frequency of which is equivalent to the Doppler shift between the incident and scattered light, and is thus proportional to the component of particle velocity that lies in the plane of two laser beams. In other embodiments, the turbulence detector may comprise a device that operates by the thermoelectric effect due to the creation of a temperature gradient between opposed surfaces of the device. In certain embodiments, this device may comprise a Peltier device that operates by the Peltier effect, or a thermoelectric generator that operates by the Seebeck effect. In one embodiment, the thermoelectric generator or Peltier device would be heated above the ambient temperature of the test chamber. This thermoelectric generator or Peltier device would produce a voltage as a function of the fluid velocity passing over its surface. This is due to the internal thermal gradient produced within the thermoelectric generator or Peltier device by the forced flow convective heat transfer from the device to the flowing fluid.

Figure 3:
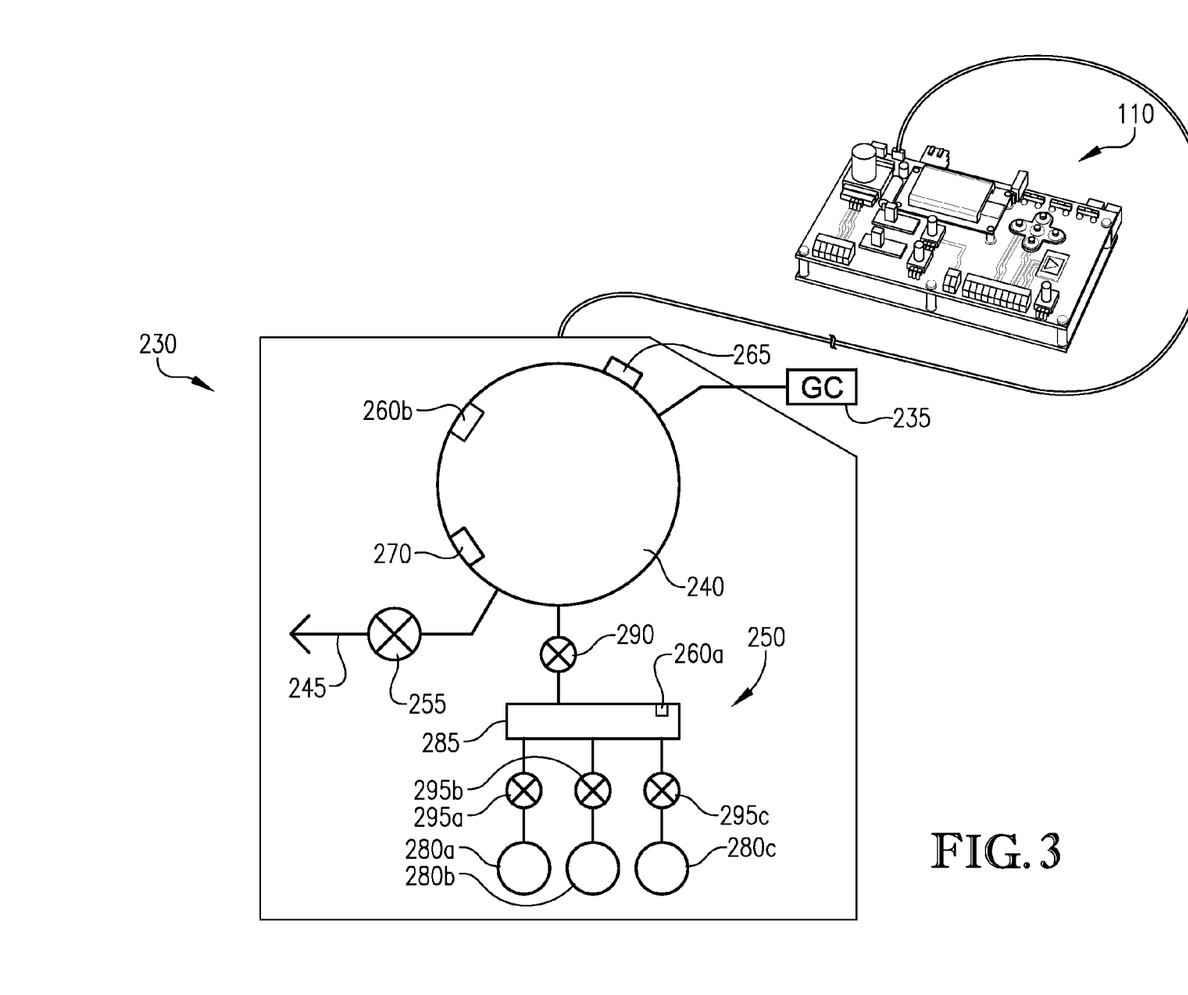
FIG. 3 is a schematic depiction of an alternate system for providing improved testing of exposibility of gaseous fuels in accordance with another embodiment of the present invention.

FIG. 3 depicts an alternate embodiment of a combustion vessel 230 that is configured for testing the explosibility of gaseous fuels. As used herein, the term "gaseous fuel" refers to various combustible materials that exist in a purely gaseous state under the testing conditions as well as combustible materials that comprise aerosols, fogs, or mists of fine, discrete liquid droplets suspended in a gaseous medium. Exemplary gaseous fuels include various hydrocarbon materials such as methane, ethane, ethylene, acetylene, propane, and propylene, other organic materials such as various alcohols (e.g., methanol, ethanol, propanol), ethers, ketones. Combustion vessel 230 is provided with a gaseous fuel discharge reservoir module 250, which may be equipped with one or more discharge reservoirs 280*a-c* that can be charged with the fuel to be tested. In certain embodiments, one of discharge reservoirs, e.g., 280*c*, can be charged with an inert purge gas such as nitrogen or argon, and used as explained in further detail below.

Reservoirs 280*a*-280*c* are fluidly coupled with a gas mixing manifold 285 via respective valves 295*a-c*. Manifold 285 permits mixtures of multiple gaseous fuels to be safely prepared prior to being introduced into test chamber 240, which includes an ignition module 270. The gaseous fuel mixture may be prepare by selectively opening valves 295*a* and 295*b*, for example, so as to introduce a desired amount of each fuel into manifold 285. A pressure sensing device 260*a* can be located within manifold 285 to assist with charging the manifold with desired amounts of each gaseous fuel. Once prepared, the gaseous fuel mixture can be introduced into test chamber 240 by opening valve 290. However, prior to introducing the gaseous fuel mixture into test chamber 240, the test chamber may be evacuated by opening valve 255 that is coupled to a vacuum source 245, such as a vacuum pump.

Once test chamber 240 is charged with the gaseous fuel mixture, remote device 110 can instruct closure of valve 290 and activation of ignition module 270. The change in pressure within test chamber 240 can be measured by pressure sensor 260*b* (which may comprise more than one actual pressure sensor). In additional, an optional turbulence detector 265 may be installed in combustion vessel 230 in order to further control activation of ignition module 270. Combustion vessel 230 may also be operably connected to a gas chromatograph device 235 so as to verify the composition of the gaseous mixture within test chamber 240 both pre-ignition and post-ignition.

Figure 4:
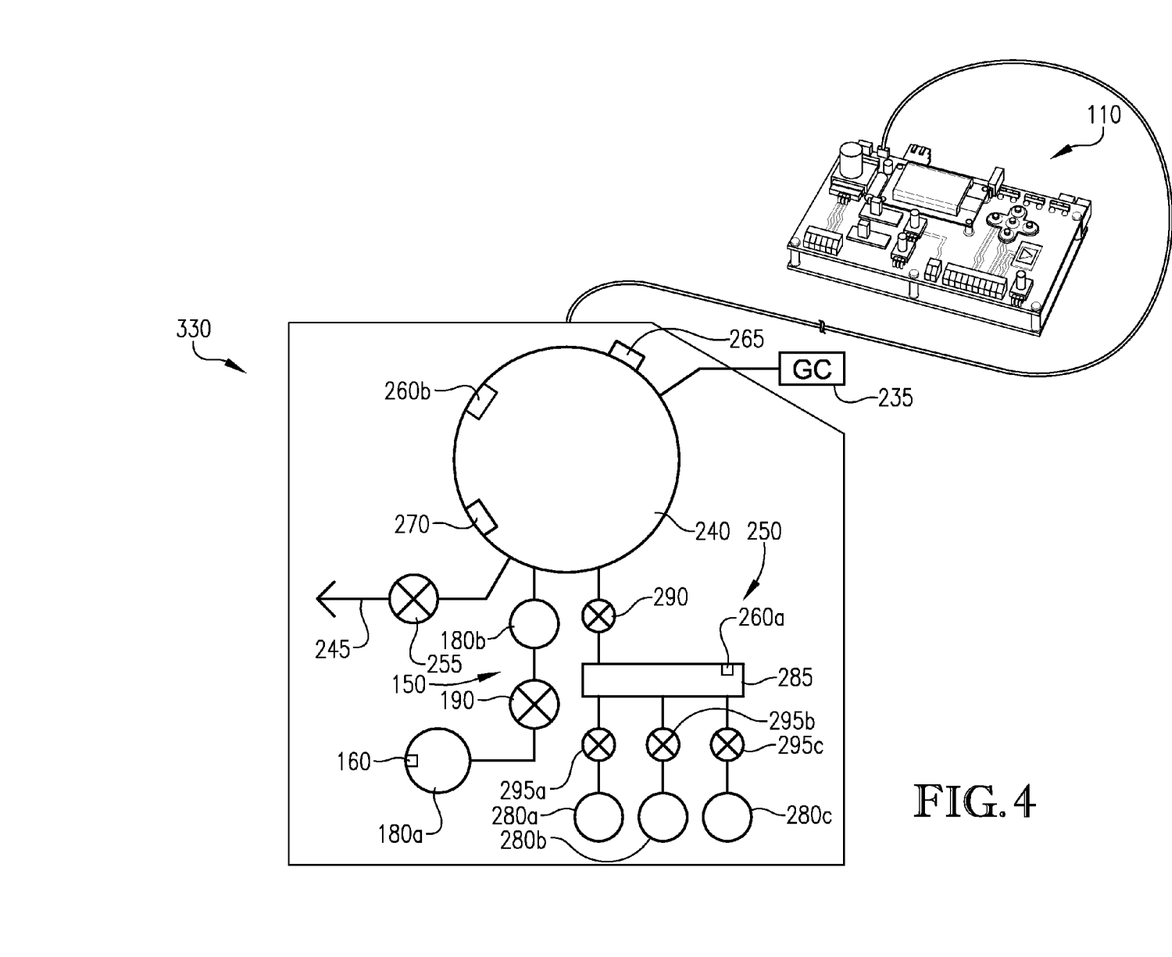
FIG. 4 is a schematic depiction of an alternate system for providing improved testing of explosibility of dust and gaseous fuels in accordance with another embodiment of the present invention.

FIG. 4 illustrates a further embodiment of the present invention, namely a combustion vessel 330 that is configured to test the explosibility of dust fuel and/or gaseous fuels. In particular, combustion vessel 330 is a hybrid of the embodiments shown in FIGS. 2*b* and 3 and comprises structure for the separate handling of dust and gaseous fuels, namely a dust fuel discharge reservoir module 150 and a gaseous fuel discharge reservoir module 250. Each of modules 150, 250 may be configured as described above and include structure for separately introducing dust and gaseous fuels into test chamber 240. It is noted that not only is combustion vessel 330 capable of individually testing either dust fuels or gaseous fuels, but mixtures of dust and gaseous fuels may also be tested. In one embodiment, the testing of such mixtures may be accomplished by first charging test chamber 240 with the gaseous fuel by opening valve 290 while valve 190 is closed. Following achieving the desired concentration of the gaseous fuel within chamber 240, valve 290 may be closed and valve 190 may be opened. In alternate embodiments, remote device 110 may operate valves 190, 290 simultaneously so that ignition can occur at peak turbulence levels for both fuels.

The computing device processor may include microprocessors, microcontrollers, programmable intelligent computers (PICs), Apple A-series processors, Qualcomm mobile processors, other mobile device processors, or the like. The processor may also include field-programmable gate arrays (FPGAs), or other programmable logic devices (PLDs), fully-custom or semi-custom application-specific integrated circuits (ASICs), or any other device that is described by one or more code segments of a hardware description language (HDL). Further, the processor may include combinations of any of the components listed.

The memory may at least store test variables and test data. The memory may include, for example, removable and non-removable memory elements such as random-access memory (RAM), read-only memory (ROM), flash, solid state, magnetic, optical, USB memory devices, and/or other conventional memory elements, such as hard-disk drives.

The user device 100 and/or remote device 110 further include a computer program for implementing the various aspects of the invention. The computer program of the present invention is stored in or on computer-readable medium residing on or accessible by the user device 100 and/or remote device 110 for instructing the user device 100 and/or remote device 110 to operate certain steps of the present invention as described herein. The computer program preferably comprises an ordered listing of executable instructions for implementing logical functions in the user device 100 and/or remote device 110. Portions of the computer program stored on memories of the user device 100 and/or remote device 110 can be updated via a computer readable medium, a communications network 120, or a manual connection. Therefore, the discussion of the computer program herein is to be understood as all code segments, either individually or collectively, that are executed to implement the steps and features described herein.

Figure 5:
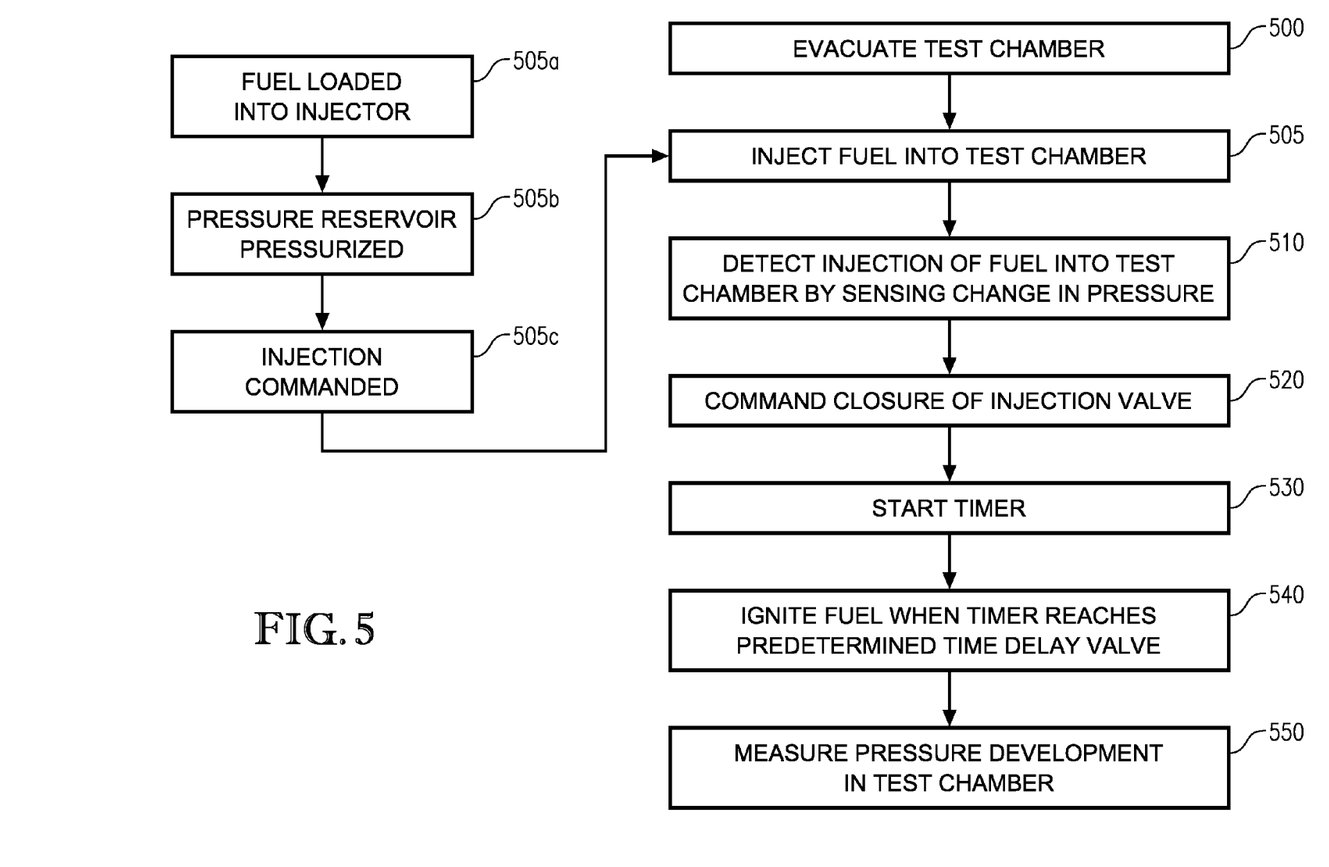
FIG. 5 is a flow chart of an improved method for testing the explosibility of dust fuels according to one embodiment of the present invention.

The computer program can be embodied in any computer readable medium for use by or in connection with an instruction execution system, apparatus, or device, and execute the instructions. In the context of this application, a "computer readable medium" can be any means that can contain, store, communicate, propagate, or transport the program for use by or in connection with the instruction execution system, apparatus, or device. The computer programs described herein can be employed with any of the combustion vessels described previously. In one embodiment, the computer program generally comprises steps as shown in FIG. 5, and the computer program is stored on a non-transitory computer-readable storage medium, wherein the program instructs a processor to perform the steps of: (1) optionally evacuate 500 a test chamber; (2) inject 505 fuel into the test chamber; (3) detect 510 the injection of the fuel by sensing a change in pressure (e.g., within the test chamber); (4) commanding closure 520 of the injection valve; (5) start 530 a timer; (6) ignite 540 the fuel when the timer reaches a predetermined time delay value; and (7) measure 550 pressure development in the test chamber. The measurement of pressure development by pressure sensors within the test chamber is directly used in the Kst value determination. In certain embodiments, particularly when a combustion vessel 130 as depicted in FIG. 2b is employed, the injecting step 505 may further comprise the steps of (1) loading 505a fuel into a fuel injector; (2) pressurize 505b a pressure reservoir; and (3) command 505c injection of the fuel into the test chamber. Although illustrated as occurring subsequent to commanding closure 520 of the injection valve, it is within the scope of the present invention for the timer to be started 530 simultaneous to or subsequent to any of the steps of injecting 505, detecting 510, and commanding closure 520. As can be appreciated, the length of time delay can be adjusted to account for the time associated with performing any intervening steps between time start and ignition 540, such as fuel injection or valve closure.

Figure 6:
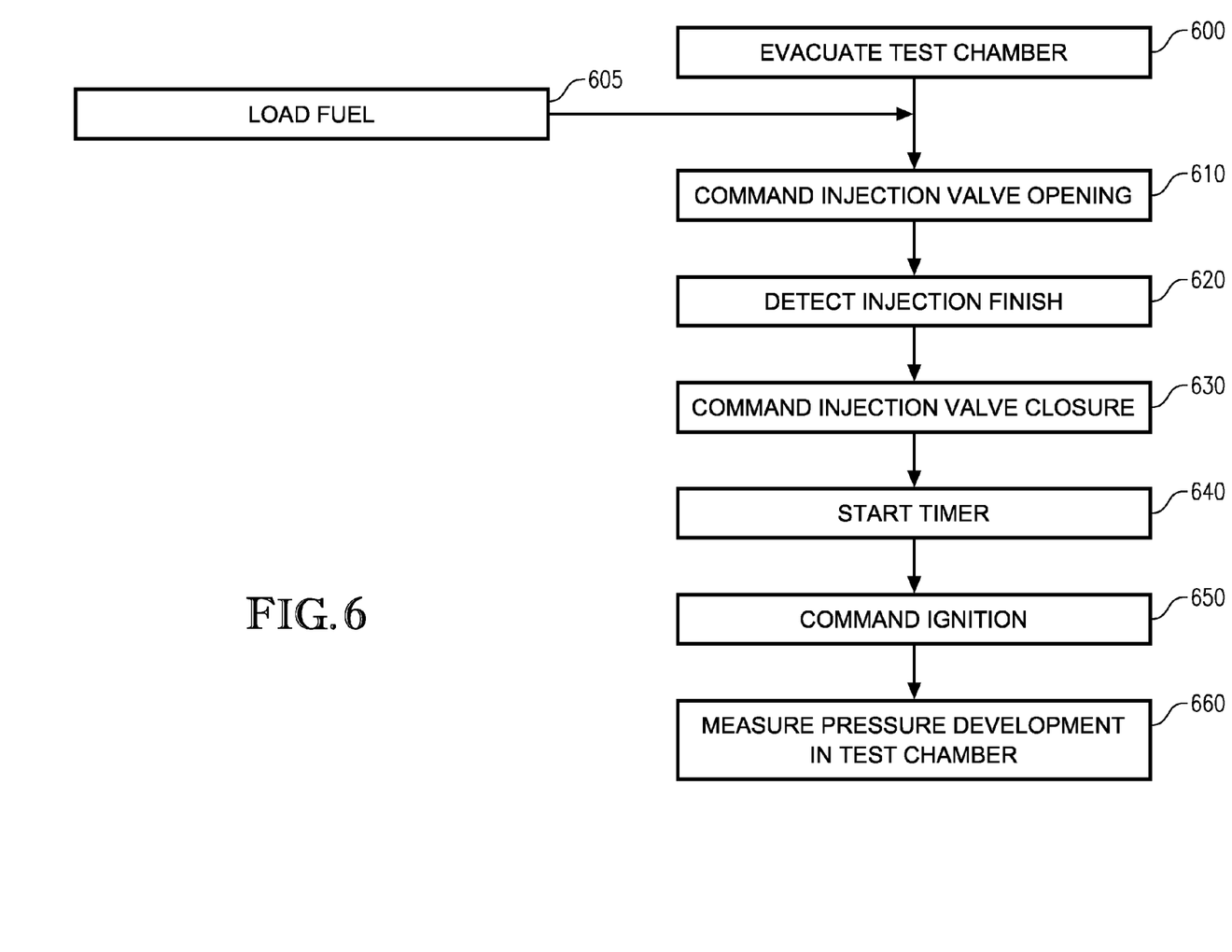
FIG. 6 is a flow chart of an alternate method for testing the explosibility of fuels according to another embodiment of the present invention.

In another embodiment, the computer program generally comprises steps as shown in FIG. 6, and the computer program is stored on a non-transitory computer-readable storage medium, wherein the program instructs a processor to perform the steps of: (1) optionally evacuate 600 a test chamber; (2) load 605 a fuel into a reservoir module, such as reservoir module 250; (3) command 610 an injection valve to open thereby causing the fuel to enter the test chamber from the reservoir module; (4) detect 620 injection finish such as through the use of a pressure sensor in the test chamber; (5) command 630 closure of the injection valve; (6) start 640 a timer (note, alternatively, that step 640 may occur simultaneous to or subsequent to any of steps 610, 620, or 630); (7) command 650 ignition of the fuel when the timer reaches a predetermined time delay value; and (8) measure 660 pressure development in the test chamber. The measurement of pressure development by pressure sensors within the test chamber is directly used in the Kst value determination.

Figure 7:
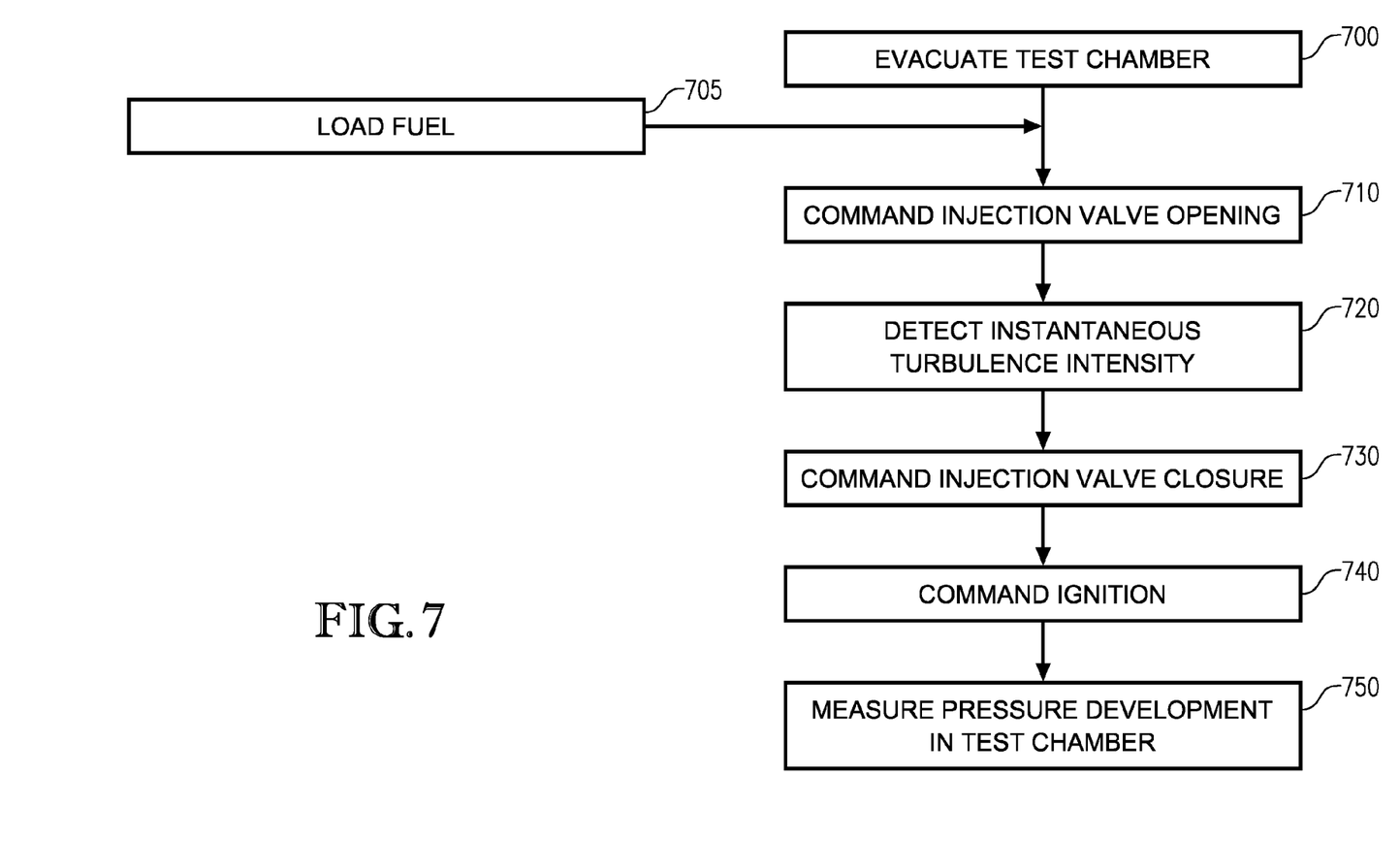
FIG. 7 is a flow chart of an alternate method for testing the explosibility of fuels according to another embodiment of the present invention in which injection valve closure is based upon turbulence intensity within the test chamber.

In another embodiment, the computer program generally comprises steps as shown in FIG. 7, and the computer program is stored on a non-transitory computer-readable storage medium, wherein the program instructs a processor to perform the steps of: (1) optionally evacuate 700 a test chamber; (2) load 705 a fuel into a reservoir module, such as reservoir module 250; (3) command 710 an injection valve to open thereby causing the fuel to enter the test chamber from the reservoir module; (4) detect 720 instantaneous turbulence intensity within the test chamber; (5) command 730 closure of the injection valve; (6) command 740 ignition of the fuel when the instantaneous turbulence intensity reaches a predetermined value; and (7) measure 750 pressure development in the test chamber. The measurement of pressure development by pressure sensors within the test chamber is directly used in the Kst value determination. Through the detection if instantaneous turbulence intensity, it can be assured that ignition occurs during the period of turbulence intensity decay, as opposed to the period in which the turbulence intensity is increasing. For example, in certain embodiments it may be desirable for ignition to occur once turbulence intensity reaches a predetermined threshold, such as 1 m/s. Predictable turbulence conditions are important for accurate Kst value determination. Therefore, it is preferable to command injection valve closure once a decay in turbulence intensity is detected and then to command ignition once the turbulence intensity has reached the predetermined threshold.

The computer readable medium can be, for example, but not limited to, an electronic, magnetic, optical, electromagnetic, infrared, or semiconductor system, apparatus, device or propagation medium. More specific, although not inclusive, examples of the computer readable medium would include the following: a portable computer diskette, a random access memory (RAM), a read only memory (ROM), an erasable, programmable, read only memory (EPROM or flash memory), and a portable compact disk read only memory (CDROM), and combinations thereof. The various actions and calculations described herein as being performed by or using the computer program may actually be performed by one or more computers, processors, or other computational devices, such as those described herein, independently or cooperatively executing portions of the computer program.

The display may comprise a graphical interface operable to display visual graphics, images, text, etc. in response to external or internal processes and commands. For example, the display may comprise conventional black and white, monochrome, or color display elements including CRT, TFT, LCD, and/or LED display devices. The display may be integrated with the user interface, such as in embodiments where the display is a touch screen display to enable the user to interact with it by touching or pointing at display areas to provide information to the user device 100 and/or remote device 110. The user input may be the press of a button or key, virtual button (including invisible or hidden virtual buttons), a swipe, gesture, motion, sound, spoken word, or any combination or plurality of the above inputs.

The present invention is an improved system for testing the explosibility of dust clouds, while satisfying testing standards under ASTM E1226-12A. Conventional combustion vessels 130 and explosibility test systems have met the ASTM testing standards, which require a repeatability accuracy of ±20% variability on Kst (the speed of the pressure rise) and ±10% variability on Pmax (the maximum pressure of a dust cloud explosion). Generally, the conventional vessels have shown a Kst variability somewhere around the range of 17-23%. Much of this variability can be attributed to delays in combustion vessel 130 component response time (e.g., actual ignition time after ignite command sent to ignition module; injection valve opening time after open valve command sent to discharge reservoir module).

Typically, when a command to inject dust fuels is initiated, a timer is initiated and begins counting towards a predetermined time delay, whereupon reaching the predetermined time delay, the dust fuels are ignited. However, in conventional systems, injection valve 190 response time variability (about 30-75 ms) is unaccounted for. Slow-responding valves may result in delayed injection times. When actual injection is delayed as a result of a slow-responding valve, the timer continues to count down towards the ignition time regardless of the time of actual injection. As discussed in the background, changes in the period between actual injection and actual ignition have a direct effect on dust fuel turbulence, which in turn, has a direct effect on Kst values. As discussed in the background, changes in the period between actual injection and actual ignition have a direct effect on dust fuel turbulence, which in turn, has a direct effect on Kst values.

Further, slow-responding valves may remain open upon the time of ignition, resulting in unintentionally varying test environments (i.e., chamber volume increased by inadvertently open dust fuel chamber). When the injection valve 190 remains open upon ignition of the dust fuels, the volume of the main test chamber can vary up to 1 liter (5% of the total system volume) during combustion. Some tests have shown that valve response times can result in up to 20% time delays from the command time to close.

The aforementioned problems are a result of two fundamental flaws in conventional testing systems. First, the timer should be configured to start upon actual injection as opposed to commanded injection. When relying solely on injection valve performance with hopes that the valve opens immediately upon command, system operators are placing an unpredictable margin of error on the test system. An injection valve is a mechanical device that is inherently limited by its mechanical structure and response time. A more accurate testing approach would be to initiate the timer upon detecting actual injection of the dust fuels.

The second problem with conventional systems is related to the inherent latency involved in time-critical calculations and decision-making performed in conventional operating systems and software. Such conventional systems have relied on multi-tasking operating systems to perform time-critical tasks such as injection valve control and ignition control. When these time-critical tasks rely on processes performed by an unmanaged and sometimes unpredictable operating system, latency can negatively influence test data by significant margins. A more reliable and accurate approach would be to include a real-time operating system with a dedicated controller for performing the aforementioned tasks.

Figure 8:
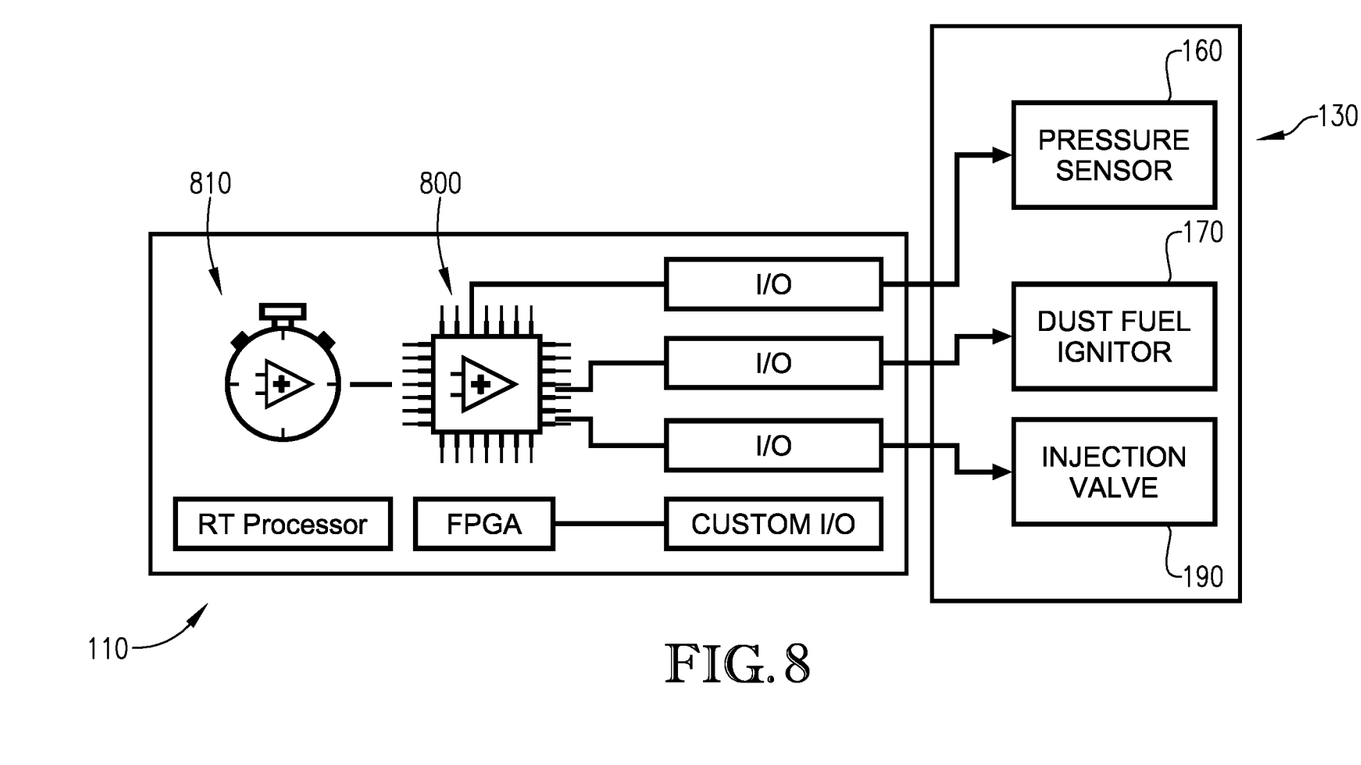
FIG. 8 is a schematic depiction of the field programmable gate array component used in a system for providing improved accuracy when testing explosibility of dust fuels in accordance with an embodiment of the present invention.

An improved combustion vessel 130 control system that utilizes a field programmable gate array (FPGA) module, as shown in FIG. 8, to observe testing conditions within the vessel and make real-time decisions based on the observations results in more accurate Kst measurements, ±3-5% variability. By eliminating the known problems of injection valve 190 response time and software latency, the herein-described improved control system can ensure that the dust fuel turbulence is consistent among a series of tests and that time-critical tasks are performed with minimal concerns of system latency.

The improved dust fuel explosibility testing system comprises a combustion vessel 130 having a test chamber 140, a pressurizable dust fuel discharge reservoir module 150, at least one pressure sensor 160, and a dust fuel ignition module 170 for igniting the dust fuel.

As previously discussed with respect to FIG. 2a, the pressurizable dust fuel discharge reservoir module 150 includes an internal dust fuel chamber 180 and an injection valve 190. The dust fuel chamber 180 is pressurized and selectively enclosed by the injection valve 190 having an open and closed state. In a preferred embodiment, the injection valve 190 is a ball valve controllable by an electronic signal, such as a command sent from a computing device 100,110. The dust fuel chamber 180 is in selective fluid communication with the test chamber 140 of the vessel when the injection valve 190 is in the open state. When the injection valve 190 is in the closed state, the dust fuel chamber 180 is generally sealed from the test chamber 140. As is generally known to one of ordinary skill in the art, in order to inject a dust fuel from the reservoir module 150 into the test chamber 140, the reservoir module dust fuel chamber 180 must be at a higher pressure than that of the test chamber 140. Injection of the dust fuel into the test chamber 140 is ultimately achieved upon opening of the injection valve 190, such that the contents of the dust fuel chamber 180, including the dust fuel, are released into the test chamber 140.

The operation of the combustion vessel 130 depicted in FIG. 2b and discussed previously is similar in many respects to the operation of the embodiment depicted in FIG. 2a. However, the discharge reservoir module 150 is configured differently. The dust fuel discharge reservoir module 150 comprises a dust fuel chamber 180b that can be charged with a dust fuel by a user. Valve 190, disposed in between discharge pressure reservoir 180a and dust fuel chamber 180b, is a ball valve controllable by an electronic signal, such as a command sent from a computing device 100,110, and especially a FPGA. Upon opening of valve 190, pressurized gas is released from discharge pressure reservoir 180a into chamber 180b. Chamber 180b is in communication with test chamber 140 such that the pressurized gas/dust mixture begins to flow into chamber 140.

Upon detection of a change in pressure within any of reservoirs 180, 180b or test chamber 140, the injection valve 190 is commanded to close immediately. The injection process creates turbulence within test chamber 140 which can significantly affect the accurate determination of Kst values. By signaling a valve-closing command substantially simultaneously with detection of dust fuel injection, turbulence within test chamber 140 is controlled and known at the time of dust fuel ignition. Stopping dust fuel injection by closing valve 190 allows the turbulence within test chamber 140 to naturally decay as a result of the viscosity of the pressurized gas. In addition, closure of injection valve 190 ensures that test chamber 140 is sealed when the dust fuel is ignited thereby preserving a constant-volume test environment. As previously indicated, a pressure sensor 160 can be located within the reservoir module such that upon an opening of the injection valve 190, a sudden decrease in pressure will trigger an indication that the injection valve 190 is to be closed. However, in the case of the embodiment depicted in FIG. 2b, one or more pressure sensors 160 can be located within the test chamber 140 such that a change in pressure, especially an increase in pressure, will trigger the indication that the injection valve 190 is to be closed. Alternatively, instantaneous turbulence intensity within chamber 140 can be determined by sensor 165 and trigger the indication that the injection valve 190 is to be closed. Other variations of the above embodiments can be implemented while staying within the scope of the present invention.

As described, the injection valve 190 is commanded to close based on a pressure change or turbulence detected by sensor 165 within some portion of the combustion vessel 130, typically either reservoirs 180, 180a or test chamber 140. By initiating closure of the injection valve 190 based on pressure or instantaneous turbulence, one can insure that predetermined time delays between injection and ignition are based on actual injection and actual ignition times. The conventional system, as described above, relies on times when instructions were sent to the components (e.g., the discharge reservoir module and ignition module). The delays in component response time invariably lead to the introduction of significant error into the test results. The improved system relies on actual injection and ignition times, providing controllable and predictable levels of turbulence, ultimately resulting to more accurate test results.

As described previously, the embodiment depicted in FIG. 3 is particularly adapted for testing of gaseous fuels and gaseous fuel mixtures. FIG. 3 is illustrated as comprising three gas reservoirs 280a, 280b, and 280c. As described previously, reservoir 280c may be reserved for an inert purge gas, if desired. The remote device 110 commands valves 295a, 295b, and 295c to selectively open and close so as to charge manifold 285 with the desired gaseous fuel(s). The remote device 110 can utilize a signal from pressure sensor 260a in order to control operation of valves 295a-c. Prior to or simultaneous with the filling of manifold 285, remote device 110 may command opening of valve 255 so that the contents of test chamber 245 can be evacuated. Following evacuation of chamber 245, valve 255 can be closed. Once the desired fuel composition is achieved within manifold 285, the remote device 110 commands the opening of injection valve 290 so that the contents of manifold 285 begin to flow into test chamber 240. Upon detecting the completion of injection, such as with pressure sensor 260b or through analysis of the fuel composition within chamber 240 by a gas chromatograph 235, remote device commands injection valve 290 to close. Subsequent to or simultaneous with closure of valve 290, remote device 110 starts a timer which provides a delay prior to remote device commanding operation of igniter 270. Alternatively, completion of injection can be determined using turbulence detector 265, which once a decay in turbulence intensity is detected, remote device instructs closure of injection valve 290. Once a predetermined intensity level has been reached, remote device 110 commands operation of igniter 270.

As described previously, the embodiment depicted in FIG. 4 is particularly adapted for testing of gaseous fuels, gaseous fuel mixtures, dust fuels, or any combination thereof. Combustion vessel 330 comprises a dust fuel reservoir module 150 and a gaseous fuel reservoir module 250. Each module is capable of independent operation by remote device 110, which permits vessel 330 to be utilized for explosibiliy testing of a wide range of fuels and fuel combinations. In certain embodiments, combustion vessel 330 may be operated as either of vessels 130, 230 described above. When desired to test a fuel mixture comprising both dust and gaseous fuels, in one embodiment test chamber 240 first may be charged with the gaseous fuel from module 250 via a command from remote device 110 to open injection valve 290. Following completion of injection of the gaseous fuel, remote device 110 commands injection valve 290 to close. Upon closure of injection valve 290, remote device 110 commands injection valve 190 to open thereby injecting the dust fuel into test chamber 240. Note, that the pressure within pressure reservoir 180a will need to be sufficiently high so as to overcome the force of the gaseous fuel already present within test chamber 240 and disperse the dust fuel therewithin. Upon detecting the completion of the dust fuel injection, remote device commands injection valve 190 to close. Subsequent to or simultaneous with closure of valve 190, remote device 110 starts a timer which provides a delay prior to remote device commanding operation of igniter 270.

In a preferred embodiment, a field programmable gate array (FPGA) module 800 is operably connected to a combustion vessel. For illustration purposes only, FIG. 8 depicts FPGA module 800 connected combustion vessel 130, although it is understood that module 800 may be connected to any combustion vessel described herein. The FPGA can be individually connected to each component (e.g., the injection valve 190, pressure sensors 160, and ignition module 170), or may be operably connected to the combustion vessel 130 having a control board configured to communicate to the aforementioned components. The field programmable gate array (FPGA) 800 is generally part of a remote computing device 110, such as an embedded controller commercially known as the sbRIO by National Instruments. The remote computing device 110 may include a real-time controller 810 and the FPGA module 800. The FPGA module 800 generally acquires data at a rate of about 5 kHz and is operable to collect samples of data (e.g., vessel pressure and discharge reservoir pressure). The field programmable gate array (FPGA) 800 is operable to process data in real-time and initiate commands (i.e. close valve after sensed pressure, or fire igniters upon timer reaching predetermined time delay) within a 1kHz clock frequency interval. Tests of the improved system have evidenced a reaction time of less than 0.001 seconds (1 ms) between the sensed pressure change within the vessel, and the field programmable gate array (FPGA) 800 detecting such change for initiating closing of the injection valve 190 and starting of an ignition delay timer. The ignition delay timer may be a software-generated timer that is embedded and controlled by the FPGA, or it can be a stand alone component operably connected to and controlled by the FPGA.

The real-time controller may include a real-time operating system that is configured to accept and respond to commands from another computing device within about 20 ms. The real-time operating system is configured to relay commands to the field programmable gate array (FPGA) 800, initiate automated tests, manually override controls, and start/stop the FPGA module 800. The real-time controller is configured to collect data from the FPGA module 800 and forward the data to a display or to another computing device via the network 120 for display or storage. The real-time controller is further configured to buffer data for transmission to another computing device. Generally speaking, the real-time controller is a standalone computing device configured with a real-time operating system and a field programmable gate array (FPGA) module 800 for time critical control of hardware components, particularly components used in dust fuel explosibility test vessels.

In a preferred embodiment, a user computing device 100 may be operably connected, via the network 120, to the remote computing device 110 (the real-time controller). The user computing device 100 may include a display for observation of data (e.g. pressure sensor 160 readings) collected by the field programmable gate array (FPGA) 800. The user computing device 100 generally serves as a control panel for initiating and observing tests from a remote location. The user computing device 100 may include any well-known operating system as described above. In contrast to the remote computing device, which requires a time-critical component (i.e., a real-time operating system and controller), the user computing device 100 generally provides the graphical user interface component for collecting and displaying lower-priority processes of the system. For example, the user computing device 100 is operable to display component operability, setting of test factors (i.e., predetermined time delays), viewing user events, displaying pressure readings, displaying prior test results, managing connections to remote computing devices, etc.

Although this invention has been described with its preferred embodiment(s), it is noted that equivalents may be employed and substitutions made herein without departing from the scope of the invention.

Having thus described various embodiments of the invention, what is claimed as new and desired to be protected by Letters Patent includes the following:

1. A non-transitory computer-readable storage medium with an executable program stored thereon for determining explosibility indices of fuels in a combustion vessel, wherein the program instructs the processor to perform the steps of:
   (1) inject fuel into a test chamber of the combustion vessel by opening an injection valve of a fuel discharge reservoir module of the combustion vessel;
   (2) detect injection of the fuel by sensing a change in pressure with one or more pressure sensors of the combustion vessel;
   (3) command the injection valve to close;
   (4) start a timer generally simultaneous to step (2); and
   (5) ignite the fuel with a dust fuel ignition module of the combustion vessel upon the timer substantially reaching a predetermined time delay value.

2. The non-transitory computer readable storage medium of claim 1, wherein the program further instructs the processor to perform the step of:
   store, in memory of a remote computing device, the predetermined time delay value,
   wherein the time delay value defines a period of time that begins upon detection of injection of the fuel into the test chamber and ends upon ignition of said fuel,
   wherein the remote computing device is operably connected to a field programmable gate array (FPGA) module,
   wherein the field programmable gate array (FPGA) module is configured to operate the timer, the fuel discharge reservoir module, the discharge reservoir pressure sensor, and the fuel ignition module.

3. The non-transitory computer readable storage medium of claim 2, wherein the program further instructs the processor to perform the steps of:
   receive the predetermined time delay value from a user on a user computing device;
   send the predetermined time delay value to the remote computing device through a network.

4. The non-transitory computer readable storage medium of claim 3, wherein the program further instructs the processor to perform the steps of:
   send the internal pressure value to the user computing device through the network;
   present the internal pressure value on a display operably connected to the user computing device.

5. The non-transitory computer readable storage medium of claim 3, wherein the network is wireless.

6. The non-transitory computer readable storage medium of claim 2, wherein the inject, detect, command to close, start and ignite steps are all initiated by the field programmable gate array (FPGA) module.

7. The non-transitory computer readable storage medium of claim 2, wherein the field programmable gate array (FPGA) module is configured to collect pressure development data from within the test chamber, the fuel discharge reservoir module, or both.

8. The non-transitory computer readable storage medium of claim 7, wherein the pressure development data collected by the field programmable gate array (FPGA) module is stored in the FPGA module, in the memory of the remote computing device, or a in a real-time controller.

9. The non-transitory computer readable storage medium of claim 6, wherein the field programmable gate array (FPGA) module initiates at least one of the steps within a 1 kHz clock frequency interval of another step.

10. The non-transitory computer readable storage medium of claim 1, wherein the injection is detected by sensing a decrease in pressure of the discharge reservoir module.

11. The non-transitory computer readable storage medium of claim 1, wherein the injection is detected by sensing an increase in pressure of the test chamber.

12. The non-transitory computer readable storage medium of claim 1, wherein the injection valve is a ball valve or a shuttle valve.

13. The non-transitory computer readable storage medium of claim 1, wherein the closing step is initiated in less than about 0.001 seconds after the injection step.

14. A method for determining explosibility indices of a fuel, the method comprising the steps of:
   (1) injecting a fuel into a test chamber by opening an injection valve;
   (2) detecting injection of the fuel into the test chamber by sensing a change in pressure;
   (3) commanding the injection valve to close;
   (4) starting a timer generally simultaneous to step (2); and
   (5) igniting the fuel upon the timer substantially reaching a predetermined time delay value.

15. The method of claim 14, wherein the time delay value defines a period of time that begins upon detecting injection of the fuel into the test chamber and ends upon igniting said fuel.

16. The method of claim 14, wherein the fuel is a dust fuel, and wherein the injecting step is performed by loading said dust fuel into a dust fuel injector of a pressurizable discharge reservoir module, pressurizing a discharge reservoir of the pressurizable discharge reservoir module, and commanding an injection valve of the pressurizable discharge reservoir module to open.

17. The method of claim 14, wherein the detecting injection step is performed by sensing a decrease in pressure of the discharge reservoir module.

18. The method of claim 14, wherein the detecting injection step is performed by sensing an increase in pressure of the test chamber.

19. The method of claim 14, wherein the igniting step is performed using an igniter module.

20. The method of claim 19, wherein the igniter module is an ignition source selected from the group consisting of a heated coil, chemical igniters, a spark generator, and a flame generator.

21. The method of claim 14, wherein the detecting step and the commanding injection valve closure step are performed substantially simultaneously.

22. The method of claim 14, wherein the commanding injection valve closure step and the starting step are performed substantially simultaneously.

23. The method of claim 14, wherein the injection valve is a ball valve or a shuttle valve.

24. The method of claim 14, wherein the closing step is initiated in less than about 0.001 seconds after the injecting step.

25. The method of claim 14, wherein said method further comprises, after igniting the fuel, measuring pressure development within the test chamber.

26. A system for determining explosibility indices of a fuel, the system comprising:
   one or more combustion vessels, each combustion vessel including—
      a test chamber;
      a fuel discharge reservoir module having an injection valve,
      at least one pressure sensor, and
      a fuel ignition module for igniting the fuel;
   one or more corresponding remote computing devices, each remote computing device including—
      a processor and a memory for storing at least a time delay value,
      a network interface module, and
      a field programmable gate array (FPGA) module operating a timer and operably connected to the test chamber,
   wherein the field programmable gate array (FPGA) is configured to instruct the fuel discharge reservoir module to open the injection valve so that fuel is released into the test chamber,
   wherein upon the at least one pressure sensor sensing a change in pressure, the field programmable gate array (FPGA) is configured to instruct the fuel discharge reservoir module to close the injection valve,
   wherein upon instructing the fuel discharge reservoir module to open the injection valve or upon the at least one pressure sensor sensing the change in pressure or upon instructing the discharge reservoir module to close the injection valve, the field programmable gate array (FPGA) is configured to start the timer,
   wherein upon the timer reaching the time delay value, the field programmable gate array (FPGA) is configured to activate the dust fuel ignition module thereby igniting the fuel.

27. The system of claim 26, further comprising:
   a user computing device operable to at least receive test commands including at least the time delay value from a user, the user computing device including—
      at least one input device operable to capture test commands,
      a processor and a memory, and
      a network interface module,
   wherein the user computing device and the one or more remote computing devices are configured to be in communication with each other over the network through their respective network interface modules,
   wherein upon capturing the test commands on the user computing device, the test commands are operably sent to the one or more remote computing devices.

28. The system of claim 26,
   wherein the field programmable gate array (FPGA) module is configured to instruct the fuel discharge reservoir module to close the injection valve within at least a 1 kHz clock frequency interval from the at least one pressure sensor sensing a change in pressure.

29. The system of claim 26,
   wherein the field programmable gate array (FPGA) module is configured to instruct the fuel discharge reservoir module to close the injection valve less than about 0.001 seconds after the at least one pressure sensor sensing a change in pressure.

30. The system of claim 26,
   wherein the user computing device further includes a display for displaying conditions of the combustion vessel.

31. The system of claim 26,
   wherein the pressurizable fuel discharge reservoir module has a greater pressure than the test chamber prior to opening of the injection valve.

32. The system of claim 26,
   wherein one or more of the at least one pressure sensors is configured to sense a decrease in pressure within the fuel injection module.

33. The system of claim 26,
   wherein one or more of the at least one pressure sensors is configured to sense an increase in pressure within the test chamber.

34. The system of claim 26,
   wherein the field programmable gate array (FPGA) module is capable of acquiring data at at least a rate of 5 kHz.

35. The system of claim 26,
   wherein the one or more remote computing devices are operable to buffer data for transmission to the user computing device.

36. The system of claim 26,
   wherein the field programmable gate array (FPGA) module is configured to collect pressure development data from the test chamber, the discharge reservoir module, or both.

* * * * *